United States Patent
Roh et al.

(10) Patent No.: US 10,517,681 B2
(45) Date of Patent: Dec. 31, 2019

(54) ARTIFICIAL INTELLIGENCE GUIDANCE SYSTEM FOR ROBOTIC SURGERY

(71) Applicant: NavLAB, Inc., Seattle, WA (US)

(72) Inventors: Jeffrey Roh, Seattle, WA (US); Justin Esterberg, Seattle, WA (US)

(73) Assignee: NavLAB, Inc., Seattle, WA (US)

( * ) Notice: Subject to any disclaimer, the term of this patent is extended or adjusted under 35 U.S.C. 154(b) by 0 days.

(21) Appl. No.: 16/288,077

(22) Filed: Feb. 27, 2019

(65) Prior Publication Data

US 2019/0262084 A1    Aug. 29, 2019

Related U.S. Application Data

(60) Provisional application No. 62/636,046, filed on Feb. 27, 2018.

(51) Int. Cl.
  *A61B 34/20* (2016.01)
  *G16H 40/60* (2018.01)
  *G06N 3/08* (2006.01)
  *A61B 90/00* (2016.01)
  *G06N 20/00* (2019.01)

(52) U.S. Cl.
  CPC .............. *A61B 34/20* (2016.02); *G06N 3/08* (2013.01); *G16H 40/60* (2018.01); *A61B 90/361* (2016.02); *A61B 2034/2074* (2016.02); *G06N 20/00* (2019.01)

(58) Field of Classification Search
  CPC combination set(s) only.
  See application file for complete search history.

(56) References Cited

U.S. PATENT DOCUMENTS

| | | | | |
|---|---|---|---|---|
| 8,830,224 B2* | 9/2014 | Zhao | ............... | G06T 11/00 |
| | | | | 345/419 |
| 8,900,131 B2* | 12/2014 | Chopra | ............ | A61B 1/00009 |
| | | | | 600/117 |
| 9,283,675 B2* | 3/2016 | Hager | ............... | B25J 9/1671 |
| 9,402,690 B2* | 8/2016 | Zhao | ............... | G06T 11/00 |
| 9,699,445 B2* | 7/2017 | Hoffman | ............ | A61B 1/00039 |
| 9,826,904 B2* | 11/2017 | Valdastri | ............ | A61B 5/11 |
| 9,855,103 B2* | 1/2018 | Tsekos | ............ | A61B 34/30 |
| 2013/0211421 A1* | 8/2013 | Abovitz | ............ | A61B 34/25 |
| | | | | 606/130 |
| 2016/0030115 A1* | 2/2016 | Shen | ............ | B25J 9/1676 |
| | | | | 606/130 |
| 2017/0265943 A1* | 9/2017 | Sela | ............ | G06F 19/00 |
| 2018/0338806 A1* | 11/2018 | Grubbs | ............ | A61B 34/30 |
| 2018/0368930 A1* | 12/2018 | Esterberg | ............ | A61B 34/76 |

(Continued)

*Primary Examiner* — Anand P Bhatnagar
(74) *Attorney, Agent, or Firm* — Perkins Coie LLP

(57) ABSTRACT

This invention is a system and method for utilizing artificial intelligence to operate a surgical robot (e.g., to perform a laminectomy), including a surgical robot, an artificial intelligence guidance system, an image recognition system, an image recognition database, and a database of past procedures with sensor data, electronic medical records, and imaging data. The image recognition system may identify the tissue type present in the patient and if it is the desired tissue type, the AI guidance system may remove a layer of that tissue with the end effector on the surgical robot, and have the surgeon define the tissue type if the image recognition system identified the tissue as anything other than the desired tissue type.

21 Claims, 6 Drawing Sheets

(56) References Cited

U.S. PATENT DOCUMENTS

2019/0110855 A1\* 4/2019 Barral .................... A61B 90/37
2019/0122330 A1\* 4/2019 Saget .................... G06T 3/0081
2019/0133693 A1\* 5/2019 Mahfouz ................ A61B 34/20

\* cited by examiner

ARTIFICIAL INTELLIGENCE GUIDANCE SYSTEM FOR ROBOTIC SURGERY

CROSS REFERENCE TO RELATED APPLICATION

This application claims the benefit of U.S. Patent Application No. 62/636,046 filed Feb. 27, 2018, entitled "Artificial Intelligence Guidance System for Robotic Surgery," which is incorporated by reference herein in its entirety.

FIELD OF THE DISCLOSURE

The present disclosure is generally related to robotic surgery and more specifically to surgery utilizing artificial intelligence to operate a surgical robot (e.g., to perform a laminectomy), further including an artificial intelligence guidance system leveraging an image recognition system.

BACKGROUND

As far back as 3,500 years ago, Egyptian doctors were performing invasive surgeries. Even though our tools and knowledge have improved since then, until very recently surgery was still a manual task for human hands.

About 15 years ago, Intuitive Surgical's da Vinci surgical robot was a new surgery device, that is routinely used to help surgeons be more precise, especially to remove natural hand tremors during surgery.

Since Intuitive Surgical's da Vinci surgical robot arrival, there have been many other surgical robots introduced. Today we are in a new wave of innovation that is best characterized by the convergence of surgical robotics with artificial intelligence (AI) and data gathered from robotic systems. We are now "digitizing" surgery by collecting and analyzing data passing through these robotic systems, such as in-motion tracking, capturing images, etc. This then allows for enhancements to the surgical processes.

For example, minimally invasive spine surgery has recently been advanced with the use of endoscopes, with innovations in the imaging equipment and advances in medical robotics. Advantages thankfully are to the patient with less pain, smaller incisions, fewer complications and rapid return to normal activity as compared to conventional surgery. Surgeons are now able to remove a ruptured disc with a very small endoscope and repair a painful disc with the aid of a miniature camera and incisions no larger than 0.5 inch. Robotics and computers are now playing an expanding role in assisting the surgeon in these minimally invasive procedures where the surgeon sits at a station peering at a monitor that shows a magnified view of the surgical field. A computer mimics and enhances the surgeon's hand movements. The computer in this instance makes the movements more precise by dampening even a tiny tremor in the surgeon's hands, which might increase the difficulty in performing procedures under high power microscopic magnification. Even with the robot enhancing the surgeon's ability, a great deal of practice is required to master the technique.

Robots are also used to help in performing tasks that may be fatiguing for surgeons. This idea formed "AESOP" which is a natural language voice-activated robotic arm that holds the camera and endoscope assembly for the surgeon during an endoscopic procedure. This innovation reduces the need for a person to be required to do this task and improves the result by moving precisely where the surgeon commands the robot, providing a steady image.

Computers are also being used in image guidance systems to give the surgeon real-time images and allow him to navigate to the specific location on the spine. The surgeon can use digital information obtained before surgery such as MRI or CAT scans or use real-time fluoroscopic x-rays to develop a three-dimensional image of the spine with the exact location of a probe placed on the spine. This technology has been shown to minimize errors in placement of pedicle screws that are sometimes used to fix the spine. It is also expected that this technology will expand to allow more precise targeting of the problem with minimal incisions and fewer surgical complications.

The use of robotics and computers in minimally invasive spine surgery has resulted in more accurate surgical procedures, shortened operative time and fewer complications. It is expected that Computer-Enhanced Image Guidance Systems will improve the precision of these procedures because of real-time 3-D imaging at the time of the surgery. Diagnostic studies will be digitally transmitted to the operating room and projected to monitors to further aid the surgeon in performing the correct procedure with minimal trauma to the patient.

Today there are basically three types of AI used for surgery. The first is by IBM in its Watson System, which uses an expert-system type of AI. Watson stores vast medical information and gives responses to natural language queries from surgeons. Watson becomes an intelligent surgical assistant.

Second is "machine learning" algorithms. These algorithms use unsupervised pattern matching algorithms that would aid doctors in recognizing when a sequence of symptoms results are matched to a similar pattern of a particular previous surgical issue or result. This will help surgeons have a learning machine at their side.

Third are technologies like "AlphaGo" that trains itself by taking data and training itself to find its own patterns. All the surgical data and outcomes are created and AlphaGo will do the surgeries virtually itself to see if it can first replicate results and then later improve results.

Traditional methods of robotic surgery have not yet embraced AI in specific areas, such as spinal surgery where AI is being leveraged for image recognition through the procedure. Therefore, novel methods are needed to leverage artificial intelligence to improve outcomes for robotic surgery, such as minimally invasive robotic spinal surgery procedures.

The subject matter discussed in the background section should not be assumed to be prior art merely because of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
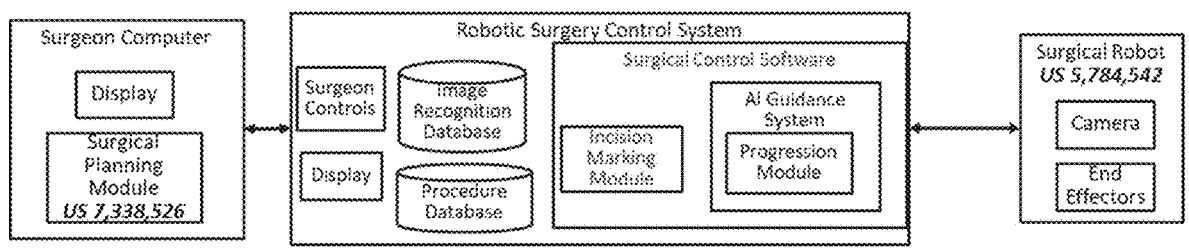
FIG. 1 illustrates a robotic surgery system and a method of utilizing artificial intelligence, according to an embodiment.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings, and in which example embodiments are shown. Embodiments of the claims may, however, be embodied in many different forms and should not be construed as limited to the embodiments set forth herein. The examples set forth herein are non-limiting examples and are merely examples among other possible examples.

Advancements in real-time image recognition systems (You Only Look Once: Unified, Real-Time Object Detection) make it possible to identify the type of tissue in front of a surgical robot's end effector. For example, this inventive system may utilize one of many available surgical planning systems to chart out the steps in the procedure for the current patient. At each step of the procedure, the desired tissue to be affected by the surgical robot's end effector(s) is defined in the surgical plan. The end effectors can include, without limitation, robotic grippers, cutting instruments (e.g., scalpels), cannulas, reamers, rongeurs, scissors, drills, bits, or the like. The degrees of freedom, sizes, and functionalities of the end effectors can be selected based on the procedure to be performed. For example, one end effector can be used to cut and remove bone and another end effector can be used to remove cartilage, discs, or the like. A series of end effectors can be used to perform a surgical procedure according to the surgical plan.

The system may take an image of the point of interest (area to be worked on in this step in the surgery) and send that image through an image recognition system. If the desired tissue type is identified by the system, the progress through the surgical step may be calculated by comparing the number of layers of tissue affected by the robot in the current procedure to the average number of layers effected to complete this surgical step in statistically similar patients who had the same procedure. That progress is displayed for the surgeon, the tissue is affected as prescribed in the surgical plan and the process repeats until the desired tissue type is not identified by the image recognition system. When the desired tissue type is not identified, the robot stops its progress and the image is presented to the surgeon to define. If the surgeon defines the tissue as the desired type, the identified image library in the image recognition database is updated and the robot proceeds.

In some embodiments, the system may obtain one or more images of a region of interest, and the images can be sent to an image recognition system. The images can be still images or video. If targeted tissue is identified by the system, a surgical plan can be generated. For example, the targeted tissue can be identified by comparing the one or more images to reference images. The comparison can be used to identify tissue to be removed, determine when a procedure is completed, etc. In some embodiments, the targeted tissue can be identified by comparing the number of layers of tissue affected by the robot in the current procedure to reference data (e.g., the average number of layers effected to complete this surgical step in statistically similar patients who had the same or similar procedure). That progress is displayed for the surgeon, the tissue is affected as prescribed in the surgical plan and the process repeats until the targeted tissue has been removed. The robot then stops its progress and the image is presented to the surgeon to define. If the surgeon defines the tissue as targeted tissue, the identified image library in the image recognition database is updated and the robot proceeds. This process can be applied to each individual step in the spinal surgery process as detailed herein.

In certain embodiments, systems and methods can utilize artificial intelligence to operate one or more surgical robot systems, including a surgical robot apparatus, an artificial intelligence guidance system, an image recognition system, an image recognition database, and/or a database of past procedures with sensor data, electronic medical records, and/or imaging data. The image recognition system may identify the tissue type present in the patient. If it is the desired or targeted tissue type, the AI guidance system may remove that tissue using an end effector on the surgical robot. The surgeon can define the tissue type if the image recognition system identified the tissue as anything other than the desired tissue type to perform a procedure. The system can identify anatomical features, abnormalities, tissue margins, tissue characteristics, tissue types, tissue interfaces, or combinations thereof based on, for example, preset criteria, physician input, etc. For example, the image recognition system can evaluate images to identify landmarks and generate a surgical plan based, at least in part, on those landmarks. The landmarks can be identified by the system, physician, or both. In some procedures, the landmarks can be identifiable anatomical features (e.g., spinous processes, bony protrusions, facet joints, nerves, spinal cord, intervertebral disc, vertebral endplates, etc.) along the patient's spine to generate a surgical plan.

In certain embodiments, systems and methods can use images obtained prior to and/or during surgery to guide a robotic surgical apparatus, end effector, surgical tool, or the like. Illustratively, an endoscope can be used as a guide wire. The endoscope can constantly interact with the anterior-posterior (AP) view, allowing a surgeon to be constantly looking at the endoscope. This system can be expanded to cover the entirety of the surgical procedure. Using the endoscope to function as a guide wire allows for locating the endoscope inside of the patient as an additional reference point for the surgical navigation program. The configuration of the endoscope can be selected based on the instrument to move delivered over it.

In certain embodiments, systems and methods can monitor a patient's brain activity during surgery to determine a level of consciousness, patient response during a procedure, or the like. For example, using of a wireless EEG system during surgery can provide a basis for determining the amount of medication to give a patient. The EEG can track the amount of discomfort the patient is experiencing, and more medication (i.e., anesthesia) can be administered if the amount of discomfort exceeds a threshold. The system can include an artificial intelligence unit that receive monitored brain activity data (e.g., brain activity patterns, brain activity spikes, etc.) and identify correlations with anesthesia based adverse events. Pain, discomfort, and other patient parameters can be monitored and evaluated to determine whether to modify the treatment plan, administer anesthesia, etc. The AI/machine learning can be used to analyze brain activity, patient feedback, or other patient parameters to, for example, improve safety, comfort, or the like.

In certain embodiments, systems and methods can include the measuring of various parameters associated with an end effector before, during, and/or after a surgical action or procedure. The monitored parameters can include rpms, angle, direction, sound, or the like. The monitored parameters can be combined with location data, tissue type data, and/or metadata to train an artificial intelligence system for guiding a robotic surgical tool to automatically perform a surgical action, procedure, or an entire surgery.

In some embodiments, a method implemented in a computing system for at least partially controlling a robotic surgical apparatus to perform surgical actions by obtaining a first image of a region of interest associated with a subject. A type of tissue shown in the first image can be identified based, at least in part, on a neural network model trained on an image training set. In response to determining that the identified type of tissue belongs to a set of targeted types, causing the robotic surgical apparatus to perform a first surgical action with respect to the region of interest in accordance with a surgical plan. A second image of the region of interest can be obtained after completion of the first surgical action. Additionally surgical steps can be performed.

A computer-readable storage medium storing content that, when executed by one or more processors, causes the one or more processors to perform actions including obtaining first image of a region of interest associated with a surgery subject, and identifying a type of tissue shown in the first image based, at least in part, on a neural network model. In response to determining that the identified type of tissue belongs to a set of targeted types, robotic surgical apparatus performs a first surgical action with respect to the region of interest in accordance with a surgical plan. A second image of the region of interest is obtained after completion of the first surgical action. The actions can include displaying types of tissue comprises displaying one or more boundary indicators for indicating at least one of targeted tissue to be removed, protected tissue, delivery instrument placement, or an end effector working space within the subject.

FIG. 1 illustrates a robotic surgery system and a method of utilizing artificial intelligence to complete specific steps in a minimally invasive surgery, according to an embodiment. The system may include a surgeon computer, a surgical robot, and a robotic surgery control system.

The surgeon computer, which can also be a mobile device, may include a display and a surgical planning module.

The surgical planning module allows the surgeon to create a plan for a robotic surgery procedure that is based upon the medical imaging of the patient, such as described in U.S. Pat. No. 7,338,526.

The surgical robot, such as described in U.S. Pat. No. 5,784,542, may include at least one camera and multiple end effectors.

The robotic surgery control system may include surgical control software, surgeon controls, a display, an image recognition database, a procedure database and a medical image database.

The procedure database can include medical records data, images (e.g., pre- and post-surgical images), physician input, sensor data, or the like. The images can include MRI or CAT scans, fluoroscopic images, or other types of images. The sensor data can be collected during procedures, etc. related to all procedures of this type. This database is queried by the surgical control for all medical imaging from the current patient and by the progression module for data for all similar patients who had the same procedure.

The image recognition database is populated by images taken by the surgical robot cameras that are defined by the surgeons and updated with each use of the system for greater accuracy. The surgeon controls are used for manual manipulation of the surgical robot, either to take over when the AI cannot proceed or to navigate the end effector to the point of interest.

The surgical control software may include an incision marking module, and an AI guidance system that may include a progression module. The surgical control software begins when initiated by the surgeon.

The pre-operative plan, as constructed by the user using a system such as the one described in U.S. Pat. No. 7,338,526, is retrieved from the procedure database.

The system may then initiate the incision marking module which will ensure the patient is properly positioned and the incision site is marked. When the incision marking module is complete the AI guidance system may be initiated. The incision marking module may be designed to cover the steps in the spinal surgery between when the patient is placed on the table and when the AI guidance system makes the first incision. The module begins when it receives a prompt from the surgical control software. The incision location, in this example just above the L4 vertebrae, is identified from the pre-operative plan. The system may then capture an image of the patient to determine if they are properly positioned on the operating table. If they are not, the surgeon or support staff are prompted for the necessary adjustment and a new image may be captured. This loop continues until the system is satisfied that the patient is properly positioned.

Next, the placement of the guide wire may be checked by the imaging system. This process loops in the same way as the patient positioning is looped. The surgeon or support staff are prompted for the necessary adjustment to the guide wire placement and another image is taken until the system is satisfied that the guide wire is properly placed. In this example, we are using a traditional guidewire, but several additional guide wire methods and systems are detailed in the attached additional embodiments of this system. When the patient position and guidewire position are correct, the system will mark the incision site.

The AI guidance system may utilize the camera to take an image of the point of interest and the progression module may compare that image to the image recognition database to determine if the tissue present is the desired tissue type that will allow the surgical robot to proceed. The progress through the tissue type is displayed based on the number of layers of the current tissue removed as compared to the average number of layers removed in other patients who had the same procedure and had a similar anatomical volume of their surgical point of interest.

In this example, the step in the spinal surgery the robotic surgical system is completing utilizing artificial intelligence is the bone removal portion of a laminectomy.

When the surgeon reaches the point in their surgical plan during which the lamina is going to be removed, the surgical robot may move a bone removal end effector to the point of interest on the patient's spine.

An imaging system connected to the image recognition software is in the same location. It can be co-located on the same robot arm as the bone removal end effector or on another mount that allows it a view of the point of interest. The imaging system may take an image of the point of interest, and the progression module will run. When the tissue type is confirmed, the bone removal end effector removes a small layer of tissue. The imaging system repeats the process of tissue type confirmation, followed by the end effector removing another layer of tissue. This loop continues until the imaging system identifies a different tissue type, ideally indicating the bone removal step is complete and the nerve tissue below has been exposed.

The imaging system and progression module are initially trained using a neural network/machine learning. Using machine learning systems which construct algorithms that can learn from and then make predictions on the image data, which is a common task in machine learning. Such algorithms work by making image data-driven predictions through building a mathematical model from image input data. The image data is used to build the final model which usually comes from multiple datasets (in this case, dataset of previous operations visual data with metadata associated with the images from doctor articulated tissue types). In particular, three data sets (images, metadata of tissue type and metadata of bone portions unfolding in the images over time) may be used in different stages of the creation of the model. A user can input or change metadata. For example, the metadata can include surgeon defined metadata. In some embodiments, the metadata can be defined by AI systems. In some embodiments, the metadata can include both user and AI defined data.

The model is initially fit on a training dataset, which is a set of examples used to fit the parameters (e.g., weights of connections between "neurons" in artificial neural networks) of the model. The model (e.g., a neural net or a naive Bayes classifier) may be trained on the training dataset using a supervised learning method (e.g., gradient descent or stochastic gradient descent). In practice, the training dataset often includes pairs of generated "input vectors" with the associated corresponding "answer vector" (commonly denoted as the target). The current model is run with the training dataset and produces a result, which is then compared with the target, for each input vector in the training dataset. Based on the result of the comparison and the specific learning algorithm being used, the parameters of the model are adjusted. The model fitting can include both variable selection and parameter estimation.

Successively, the fitted model can be used to predict the responses for the observations in a second dataset called the validation dataset. The validation dataset provides an unbiased evaluation of a model fit on the training dataset while tuning the model's parameters. Validation datasets can be used for regularization by early stopping: stop training when the error on the validation dataset increases, as this may be a sign of overfitting to the training dataset. This simple procedure is complicated in practice by the fact that the validation dataset's error may fluctuate during training, which would require added ad-hoc rules for deciding when overfitting has truly begun. Finally, the test dataset is a dataset used to provide an unbiased evaluation of a final model fit on the training data.

Once this trained dataset is built, the real-time images may be fed into the system and as tissues are identified, the tissue types are annotated virtually over the real time images, with a % probability of identification. This allows the doctor to have an AI image recognition assistant.

The system includes a failsafe that allows the surgeon on hand to stop the process. Stopping the process may include a teaching step in which the surgeon defines the tissue type visible, to improve the functionality of the image recognition software.

The failsafe system provides historical data of many operations that stores the amount of time (video) and the Virtual identified images on the tissue. The tissues identified may be in a time sequence as the operation proceeds. In a real-time operation, the sequence of image-recognized tissue (and the timing of getting to and through these recognized tissues) is compared to the historical database. If the real-time recognized tissues are correlated with the same sequence of tissues in the historical database, the system proceeds. However, if a recognized tissue does not appear in the sequence history, or if the recognized tissue appears earlier than expected, the fail system is alerted, which causes an alarm, with a virtual message over the non-normal images.

There could be other fail-safe triggers, such as (1) the length of time between recognized tissues that are normal, (2) the probability of the recognition trending down, (3) the image quality starting to degrade, etc. In this way the failsafe system could have multiple processes running simultaneously.

When the AI guidance system completes a step in its entirety, it may return to the surgical control software, which determines based on the pre-operative plan, if the procedure is complete. If the procedure is complete, the program ends.

If the program is not complete, the pre-operative plan is consulted to determine if the next surgical step requires a different end effector.

End effectors in this scenario also include tools such as retractor tubes and surgical hardware, in addition to the incision markers, bone removal tools, skin/muscle fascia incision tools, etc. If a new end effector is needed, the surgeon or support staff makes the hardware adjustment before the system proceeds to the next step in the pre-operative plan. After the needed end effector/tool is put into place, or if the same end effector/tool from the previous step is appropriate, the system may go back to the AI guidance system until the next surgical step is completed. This process continues to loop until the procedure is complete. To perform multiple procedures on a patient, the end effector can be replaced to begin another procedure. For example, one set of end effectors can be used to perform a laminectomy and another set of end effectors can be used to perform a stenosis decompression procedure at a different level along the spine.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 2:
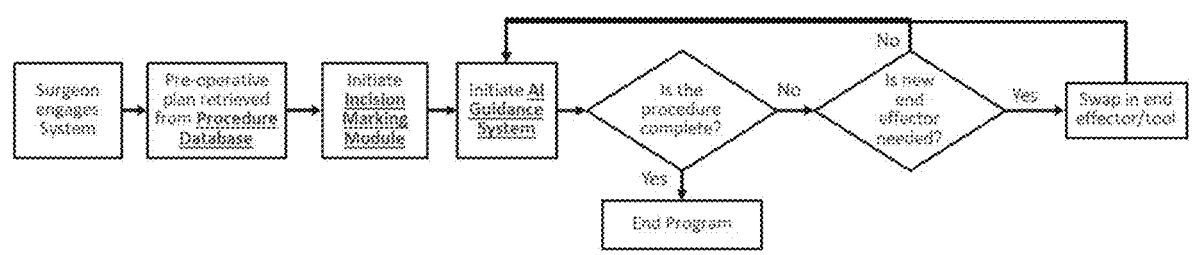
FIG. 2 illustrates a Surgical Control Software module, according to an embodiment.

FIG. 2 represents the surgical control software that is part of the robotic surgery control system, according to an embodiment. The system begins when it is engaged by the surgeon.

The pre-operative plan, as constructed by the user using a system such as the one described in U.S. Pat. No. 7,338,526, is retrieved from the procedure database.

The system may then initiate the incision marking module which will ensure the patient is properly positioned and the incision site is marked. When the incision marking module is complete, the AI guidance system is initiated.

The AI guidance system works through each step in the surgical process. In this example, we are focusing on the removal of the lamina from the L4 vertebrae, but the system is applicable to one or more steps in the spinal surgery process, from initial incision, port placement, retractor docking, lamina removal, disc removal and/or hardware insertion. The AI guidance system runs until an isolated surgical step is complete. When the AI guidance system completes a step in its entirety, it returns to the surgical control software, which determines based on the pre-operative plan, if the procedure is complete. If the procedure is complete, the program ends.

If the program is not complete, the pre-operative plan is consulted to determine if the next surgical step requires a different end effector. End effectors in this scenario also include tools such as retractor tubes and surgical hardware, in addition to the incision markers, bone removal tools, incision tools (e.g., skin/muscle fascia incision tools), etc. If a new end effector is needed, the surgeon or support staff can make the hardware adjustment before the system proceeds to the next step in the pre-operative plan. After the needed end effector/tool is put into place, or if the same end effector/tool from the previous step is appropriate, the system may go back to the AI guidance system until the next surgical step is completed. This process continues to loop until the procedure is complete.

Figure 3:
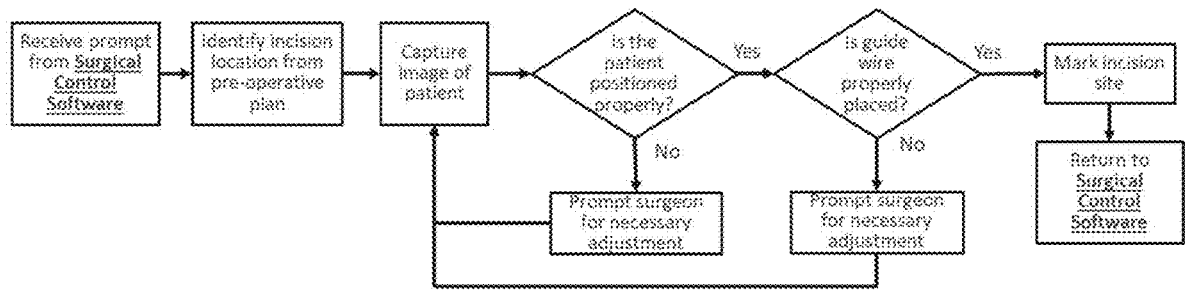
FIG. 3 illustrates an Incision Marking Module, according to an embodiment.

FIG. 3 represents the incision marking module that is part of the surgical control software, according to an embodiment. The incision marking module is designed to cover the steps in the spinal surgery between when the patient is placed on the table and when the AI guidance system makes the first incision.

The module begins when it receives a prompt from the surgical control software. The incision location, in this example just above the L4 vertebrae, is identified from the pre-operative plan.

The module may then capture an image of the patient to determine if they are properly positioned on the operating table. If they are not, the surgeon or support staff are prompted for the necessary adjustment and a new image is captured. This loop continues until the system is satisfied that the patient is properly positioned.

Next, the placement of the guide wire is checked by the imaging system. This process loops in the same way as the patient positioning is looped. The surgeon or support staff are prompted for the necessary adjustment to the guide wire placement and another image is taken until the system is satisfied that the guide wire is properly placed. In this example, we are using a traditional guidewire, but several additional guide wire methods and systems are detailed in the attached additional embodiments of this system.

When the patient position and guidewire position is correct, the system may mark the incision site. This can be done in many ways, including having the surgeon mark the site as guided by a projection from the system.

Figure 4:
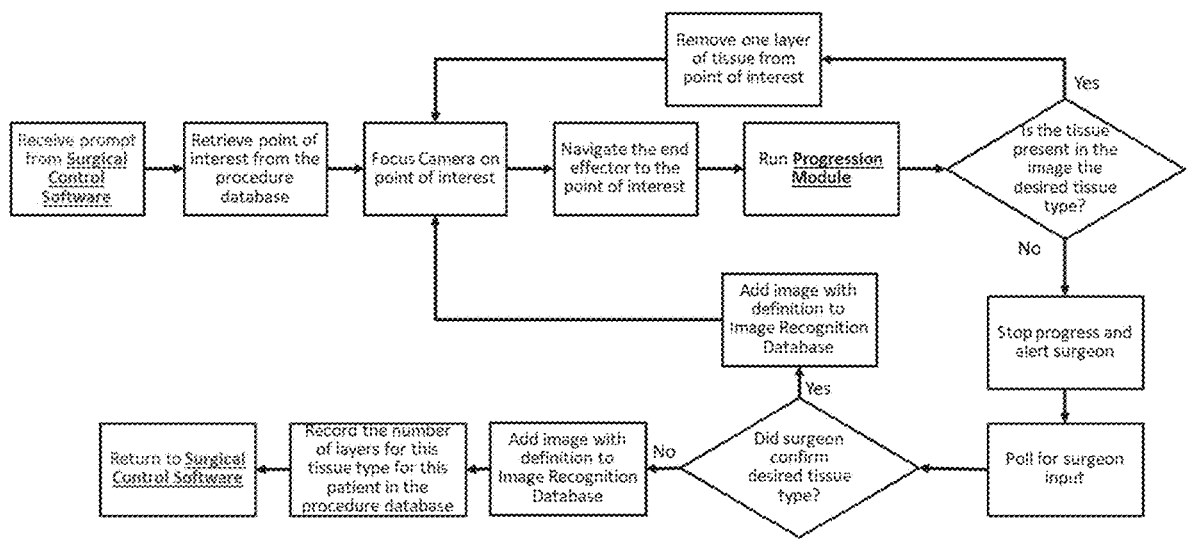
FIG. 4 Illustrates an AI Guidance System, according to an embodiment.

FIG. 4 represents the artificial intelligence (AI) guidance system. The system begins when it receives a prompt from the surgical control software. While this system may be utilized at each step in the surgical process, the example here will be the removal of the lamina from the L4 vertebrae.

The point of interest, in this example the L4 vertebrae, is identified from the procedure database. The camera(s) is focused on the point of interest.

The end effector is navigated to the point of interest.

Then the progression module is run, which may update the progress on the robotic surgery control system display and return if the tissue at the point of interest is the desired tissue type, in this example the desired tissue type is bone. So, if the tissue type identified is not bone, the system stops, alerts the surgeon and polls for their input.

The surgeon will need to define the tissue type currently at the point of interest. If the surgeon defines the current tissue type as the desired tissue type, this updates the image recognition database and the system returns to the progression module with the updated image recognition definitions. If the surgeon defines the tissue as any other type of tissue than the desired tissue type, the image definition is added to the image recognition database and the number of layers removed of the desired tissue type for the current patient is recorded in the procedure database.

Figure 5:
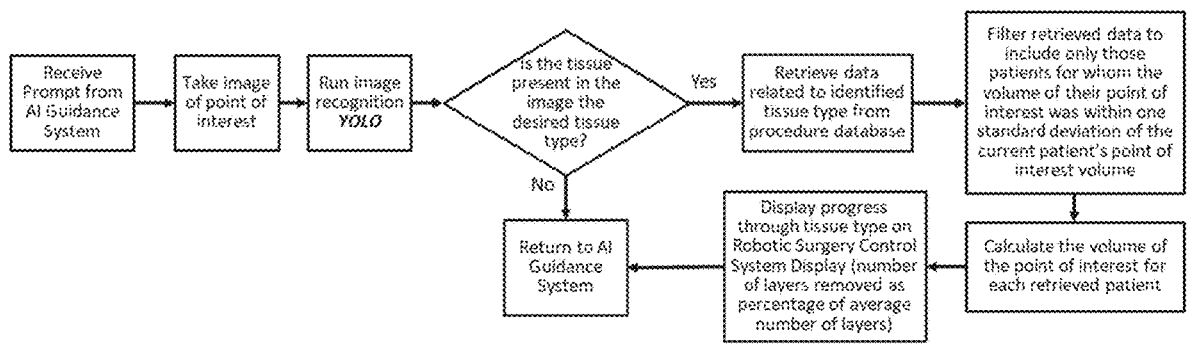
FIG. 5 illustrates a Progression Module, according to an embodiment.

FIG. 5 represents the progression module, according to an embodiment. The progression module is triggered by the AI guidance system when the imaging system and the end effector are at the point of interest on the current patient.

An image of the point of interest is taken and an image recognition system, such as described in "You Only Look Once: Unified, Real-Time Object Detection", is used to identify the tissue type present in the image taken of the point of interest on the current patient. The image recognition system utilizes the image recognition database to identify the tissue type and to store the definitions of tissue types found in images as they are defined by surgeons using the system.

You only look once (YOLO) is a state-of-the-art, real-time object detection system. Prior detection systems repurpose classifiers or localizers to perform detection. They apply the model to an image at multiple locations and scales. High scoring regions of the image are considered detections. YOLO uses a totally different approach in that it applies a single neural network to the full image. This network divides the image into regions and predicts bounding boxes and probabilities for each region. These bounding boxes are weighted by the predicted probabilities. The model has several advantages over classifier-based systems in that it looks at the whole image at test time so its predictions are informed by global context in the image. YOLO also makes predictions with a single network evaluation which makes it extremely fast, more than 1000× faster than most prior art systems.

The real-time images may be fed into a "trained neutral network image system" as described above, which uses this historical data to inform the YOLO system. The real-time images may be used to identify the tissue type present in the image taken of the point of interest on the current patient.

Unlike simply identifying the tissues types, which we have discussed above by adding a Virtual tissue tag on the images, this YOLO system goes further, in that it can detect distances and positions between the boundary boxes. In this way, tissue type will not only be defined virtually over the real-time images, but virtual distances are overlaid and can be highlighted when they are outside norms (again these distances of boundary boxes are pre-trained). The image recognition system utilizes the historical image recognition database and YOLO to identify the tissue type and their positions to provide real-time augmentation data to the surgeons using the system.

If the tissue type identified is not the desired tissue type for the surgical robot to proceed with tissue removal, the module ends and returns to the AI guidance system. If the tissue type identified is the desired tissue type to proceed with tissue removal, data related to the identified tissue type is retrieved from the procedure database. For example, if the current patient is having a laminectomy done on his L4 vertebrae, the system will retrieve all data related to laminectomies performed on the L4 of any patient in the procedure database. Those results are then filtered by the progression module based on the volume of the current patient's L4 vertebrae. This is calculated based on the medical imaging data, such as the patient's pre-surgery MRI.

The volume of the L4 vertebrae in this example is calculated for all the patient data retrieved from the procedure database. Patients for whom the volume of their L4 vertebrae is, for example, within one standard deviation of the volume of the current patient's L4 vertebrae are kept for comparison. The average number of layers removed from the desired tissue type (in this example bone) to complete this step in the procedure for the filtered patients is then calculated.

The progress of the current procedure, number of layers removed as a percentage of the average layers removed in similar patients, is displayed on the robotic surgical system display. The module then returns to the AI guidance system.

There are many improvements on the basic inventive principle describe here in many of the areas of the process.

Improvements in "Incision localization/marking" are made such as Pre-Operative Image. A user can input information for performing procedures. The information can include, without limitation, targeted tissue, non-targeted tissue, critical tissue (e.g., tissue to be protected or avoided), access paths, cutting/drilling paths, instrument orientations (e.g., delivery instruments, surgical instruments, etc.), working spaces, safety barriers, hold spots, or the like. The information can be used to determine or modify a surgical plan and can be inputted via a touch screen, keyboard, or the like. A method of using an image in which a sketch on the image indicates parts of the bone are to be removed. This is a freehand adjustment by the surgeon to the preoperative plan, layered on top of medical imaging (MRI, CT, etc.). This adjustment to the surgical plan is transmitted to the AI surgical robot and it only removes the desired area, the surgeon supervises the robot during the procedure to take over/resume the operation if necessary.

Improvements in "Incision localization/marking" are made such as Pre-Operative Image using Interactive User Interface. Similar to 1a, except the image received from the surgical robot is displayed on a touch screen/user interface inside the operating room and the surgeon sketches on the image which of the corresponding area of tissue is supposed to be removed. Other important areas can be identified (such as nerves) to warn the robot to stay away from sensitive areas. This is applicable to all steps past this one in this process but is documented here as this is the first step in which the surgeon would mark out areas during the procedure as opposed to during pre-operative planning.

"Incision localization/markings" are made as Pre-Operative Images on an actual image using Interactive User Interface. The system would deploy graphical tools, similar to power point, that allows the surgeon to draw shapes of different colors over the image. The shapes can be auto filled with the suggested colors and meta-tags (e.g., distance depth, speed of drill, amount of dither, etc.). For instance, the system could allow the surgeon in drawing mode to define the draw pen or mouse to be defined as "red, 1 mm deep, 100 rpm, +/−5 rpm", where red would correspond to drill, 1 mm deep at 100+/−5 rpm. In another area for instance, the surgeon could have defined a yellow+0.5 mm which is a region that the robot is barred from running. One could image many other user interface controls, such as (1) cutting or drilling paths, (2) degrees of safety barriers along the cutting, (3) hold spots, (4) jump to another spots, etc. The surgeon would stand by during the procedure and can turn off the machine at any time. The drill also has built-in safeguards. For example, it can detect if it's too close to a nerve (e.g., a facial nerve) and will automatically shut off.

Improvements in "Incision localization/marking" are made such as Pre-Operative Image using Interactive User Interface to Resolve Latency Issues. Like 1b, except the focus is on adjusting the field of view (zooming in) to define in greater detail where tissue barriers of interest are and what actions should be taken relative to those barriers.

Improvements in "Incision localization/marking" are made such as Multiple Imaging Systems for Problem Space Identification in Spinal Surgery. A method that combines multiple imaging systems to identify a problem space in a patient's spine. An algorithm is applied to the images to calculate the best incision location based on where the problem space is located. This algorithm accounts for the surgical procedure being used when identifying the incision site.

Improvements in "Incision localization/marking" are made such as Guide Wire Placement for Best Incision Site using a Robot. A method that enables a robot to manipulate the guide wire (i.e. adjust its length). The robot reviews an image to place the guide wire based upon best practices, which is learned through image recognition, historical data, and other sources. This method includes placing an ink tip on the guide wire that marks the location for the best incision site. This information is stored in the database, which allows the robot to access this information in following procedures. This method would increase efficiency, accuracy, and repeatability for locating incision sites.

Improvements in "Incision localization/marking" are made such as Robotic Guide Wire Placement through Surgeon Commands. A method that allows surgeons to annotate where a robot should move or adjust to in order to place the guide wire while locating an incision site. The robot can learn where it is commanded to move and store the information in a database. The robot can access this database to use for references during future procedures. This increases efficiency, accuracy, and repeatability for locating incision sites.

Improvements in "Incision localization/marking" are made such as Multi-Shaped Guide Wire. The method to create guide wires that have different, adjustable 2D shapes. This will allow the surgeon to pick the most applicable shape to use for different procedures or at a specific point in a procedure. The shapes can also be produced through the combining of different guide wires. Guidewire shape would be determined by AI using correlations between patient attributes, procedure type, wire shape, and postoperative outcomes.

Improvements in "Incision localization/marking" are made such as Imaging System Output Projection onto Patient's Skin. A method for accurately projecting an imaging system output (MRI, CT, X-Ray, Fluoroscopy, etc.) onto the patient to show where different tissue types are located underneath the skin. The projection would also include a projection of the guide wire to help the surgeon visualize the best point of incision. This increases the accuracy of the incision point. This can be done with high-speed projectors, or with an augmented reality display for the surgeon. Alternate embodiments can include virtual reality headsets for incision placement.

Improvements in "Incision localization/marking" are made such as Artificial Intelligence for Optimal Trajectory and Incision Placement for Spinal Surgery. A software that utilizes artificial intelligence to determine the optimal trajectory and incision placement for any type of spinal surgery (e.g., spinal fusion, decompression procedures, screw placement, cage insertion, etc.). This method uses information about the surgery to decide the trajectory and incision site, such as screw size, the angle the screw will be inserted at, and other information. A virtual line is then drawn out from where the drill will be placed during surgery.

Improvements in "Incision localization/marking" are made such as Incision Site Location Means based on Screw Placement Information. A means for marking the incision site for a spinal surgical procedure that includes information that cites where the screw needs to be placed, which was determined from a mathematical calculation. This information includes an image, which shows the projected incision site from an algorithm. This process will help make the incision site more accurate and the process for finding this site more repeatable, regardless of the patient's anatomy.

Improvements in "Incision localization/marking" are made such as Incision Site Location Means based on Procedure Type and Point of Interest. A means for marking the incision site for a surgical procedure based on where the surgeon's point of interest is in the patient. An algorithm is used to determine where the best incision site is on the patient based on the procedure and where the surgeon's point of interest is. This process will make the incision site more accurate and the process for finding this site more repeatable, regardless of the patient's anatomy. The amount of soft tissue damage that occurs in surgery will also decrease because the algorithm accounts for minimizing tissue damage.

Improvements in "Incision localization/marking" are made such as Imaging Port Location System using Artificial Intelligence. A system uses artificial intelligence to map where an imaging port should be located on the patient to most effectively map the patient's body. This system considers where the surgeon is planning to make the initial incision on the patient's body to help determine where the imaging port should be located. The system re-evaluates where the imaging port should be placed during different steps throughout the procedure.

Improvements in "Incision localization/marking" are made such as Virtualized Third Person Perspective of Endoscope Progress through AR/VR. A method that virtualizes a third person perspective of endoscope progress through augmented reality or virtual reality means. The third person perspective of the effort head would be mapped to other medical images used during surgery. This allows the camera point of view to be virtualized, eliminating the need to have a second entry port. This method comprising of a camera that is placed on the end effector itself, which provides a real-time image; and a tracking system shows the position of the endoscope in the patient's body from the outside in real-time. All this real-time data is overlaid on the pre-constructed model, which provides the surgeon with information that allows him or her to dynamically changed the perspective.

Improvements in "Incision localization/marking" are made such as Using Mill Image for Robot Position Confirmation and Quantifying Confirmation Level. A system that enables the computer to analyze a pre-operative MRI image using artificial intelligence to identify the patient's abnormality. This information can be used to confirm the position of a robot. This would eliminate wrong level surgery. This is augmented with a method that quantifies the confirmation level of the robot's position, acting as a "confirmation meter". This may include using many sources, such as multiple images at different levels, using pre-operative images, inter-operative images, computer-assisted navigation, and other means, to calculate the accuracy of the robot's position. The higher the position accuracy, the higher the confirmation meter score.

Improvements in "Incision localization/marking" are made such as Method of using an Endoscope as a Guide Wire. A method for designing the endoscope so that it also acts as a guide wire. This will allow the endoscope to constantly interact with the anterior-posterior (AP) view, allowing the surgeon to be constantly looking at the endoscope. This system is expanded to cover the entirety of the procedure by using the same functionality that allows the endoscope to function as a guide wire to locate the endoscope inside of the patient as an additional reference point for the surgical navigation program. The configuration of the endoscope can be selected based on the instrument to be delivered over it.

Improvements in "Initial Skin Incision" are made such as Use of Wireless EEG during Surgery to Track Patient Brain Activity. The use of a wireless EEG system during surgery to track the patient's brain activity. This would allow the surgeon to view the brain activity of the patient during surgery to know how the patient is responding the operation. For example, this would allow the surgeon to see the brain activity of patient that is not completely unconscious from anesthesia. This could indicate when the patient is experiencing a large amount of pain or excessive stimulation, signaling the surgeon to change tactics or retract. This system could be improved with real-time image recognition and artificial intelligence identifying correlations between brain activity patterns and adverse events during a procedure. This method is detailed in this step as it is the first invasive step but is applicable throughout the procedure.

Improvements in "Initial Skin Incision" are made such as Use of Wireless EEG on Patient for Medication during Surgery. The use of a wireless EEG system during surgery to help determine the amount of medication to give a patient. The EEG will track the amount of discomfort the patient is experiencing. If the patient is experiencing a large amount of discomfort or pain, the patient may be given more medication (i.e. anesthesia) during the surgery. Like 2a this system will require an artificial intelligence to examine, through a real-time image recognition system, the brain activity (e.g., brain activity patterns, brain activity spikes, etc.) and identify correlations with anesthesia based adverse events. Pain, discomfort, patient vitals, etc. can be monitored and evaluated to determine whether to modify the treatment plan, administer anesthesia, etc. The AI/machine learning can be used to analyze brain activity, patient feedback, or other patient parameters to, for example, improve safety, comfort, or the like. This method is detailed in this step as it is the first invasive step but is applicable throughout the procedure.

Improvements in "Initial Skin Incision" are made such as Pattern Recognition from EEGs during Surgery for Pre-Operative Care Improvement. A method that analyzes information collected by wireless EEGs used during surgery to use to create optimal pre-operation procedures. The data collected by the EEG about the amount of pain or discomfort experienced by the patient may be stored in a database and analyzed for patterns based on various factors including medications given, the patients' demographics, and other factors. Based on patterns found from the data, the type and amount of pre-operative medications given to future patients can be improved. This method focuses on the individual's EEG patterns in response to stimulation prior to surgery rather than a population-wide correlation generator.

Improvements in "Muscle Fascia Incision" are made such as a Method of Machine Learning to Identify Various Tissues. A method of machine learning training for an AI surgical robot in which a surgeon identifies the different types of tissues (nerve, ligament, bone, etc.) and how to use different end effectors for each type of tissue. Rules can be added to ensure that specific end effectors can only be used on specific types of tissue (i.e. a drill is only used on bone, or a nerve is only touched with a probe or not allowed to be touched at all). This is applicable to all steps in the process but documented here as multiple tissue types are involved in this specific step.

Improvements in "Muscle Fascia Incision" are made such as a Normalize Lighting for AI Image Recognition. A method of using a normalized lighting for probe or imaging system for AI image recognition, in addition, once the AI surgical robot can identify specific types of tissue a normalized lighting process will allow for the robot to see the same or similar colors to easily identify previously learned tissues.

Improvements in "Muscle Fascia Incision" are made such as Mapping of Stimulated Muscles for Surgery. A method that allows for the location of muscles inpatient to be mapped through electric stimulation, producing an image that is used for surgery. This would enable a robotic surgery to be guided with at least a first image of a patient's muscles.

Improvements in "Muscle Fascia Incision" are made such as Artificial Intelligence System for Equipment Use in a Robotic Surgery. An artificial intelligence system that uses information such as color, texture, and force to what equipment is being utilized in a robotic surgery. For example, this system will understand when enough bone has been worked through to recognize that the robot should stop using the drill. This is like the concept described in the disclosure, but rather than relying solely on image recognition, the system incorporates contact sensors, tissue type sensors (e.g., impedance sensors, optical sensors, etc.), pressure sensors, force sensors, to improve the accuracy of the tissue identification system. The system can analyze signals from the sensors to determine, for example, the force required to continue through the tissue, tissue type, texture the tissue, or the like. The system can perform procedures based, at least in part, on identifying the tissue type and its location.

As a drill or knife is robotically controlled, the drill or knife would have highly sensitive force transducers. These force transducers produce a real time X,Y,Z force set of data. The data is collected in many successful operations. The real-time images not only have all the previous metatags discussed, but also have the real time X,Y,Z force data. Now the system can be trained to show the delta force change going from one tissue type to another. As above, the change in force in X,Y,Z can be used to compare to real-time operations. If the tissues are identified correctly and within range, and the forces and changes of force are within range, the images are annotated with virtual information showing that tissues and forces and changes in force are in order. If, however, the forces or changes of force appear out of normal range, alarms would sound, and automated robotic stops would be done to investigate the out of norm situation. With this system, the surgeon can create a "sensitivity" of force change at various parts of the operations, so the system may alarm when it approaches a nerve as the force and change of force alarm is set at a more sensitive level than another part of the operation.

Improvements in "Muscle Fascia Incision" are made such as Biomarkers for Robot Communication. A system that uses biomarkers to communicate with a robot where it is during surgery. This system can recognize what type of tissue the robot is touching and then be able to mark the tissue accordingly. Using this system, a robot will be able to recognize what type of tissues it is near and use that information to determine where it is in the patient.

Improvements in "Docking of the retractor (tube) over the site of interest" are made such as AR/VR display of Surgical Device Placement During Operation. A method for using AR or VR to display where a surgical device (i.e. a screw) is being inserted into the patient. The precise display of where the device should be located can be seen by the surgeon during an operation, so the device is accurately placed. The surgical device placement recommendations are based upon the artificial intelligence's examination of surgical procedure data, patient data, and postoperative outcomes, to identify correlations between device placement and adverse events, or device placement and positive post-operative outcomes.

Improvements in "Docking of the retractor (tube) over the site of interest" are made such as Vibrating the Robotic Retractor Tube. A retractor tube that is a part of a robot that vibrates microscopically at a high speed. This would create a wavefront that would allow the tube to insert into the patient's body with greater ease. This concept would be augmented using the AI in conjunction with the image recognition system to identify tissue types and adjust the vibration frequency/amplitude based upon correlations identified by the AI between vibration frequencies/amplitudes and positive outcomes/adverse events.

Improvements in "Docking of the retractor (tube) over the site of interest" are made such as Changing the Temperature of a Retractor Tube. The same as 4b, but a means for changing the temperature of the retractor tube (i.e. heating it up or cooling it down) instead of vibration. This will allow the tube to insert into the patient's body with greater ease. This system will also benefit from the use of AI to determine the correct temperature based on tissue type/patient attributes/procedure details/etc.

Improvements in "Confirming position/level prior to planned surgical procedure" are made such as Hand-Held Ball Tip Probe Mapping Device. A method of using a hand-held ball-tip probe with sensors located in the robotic arm/surgical tool to determine the position of the ball tip probes location for creating a 3D map of a patient's spine to assist the surgeon during the operation. The sensors could use haptic feedback to determine if the ball tip probe was in contact with the spine (bone and cartilage) or soft tissue (muscles, etc.). This method is detailed in this surgical step as an example but is applicable to each surgical step.

Improvements in "Confirming position/level prior to planned surgical procedure" are made such as Hand-Held Ball Tip Probe Mapping Device Providing Haptic Feedback to Surgeon. Similar to "Handheld ball-tip probe mapping device", this is a method of using a hand-held ball-tip probe with sensors located in the robotic arm/surgical tool in order to determine the position of the ball tip probes location for the purpose of creating a 3D map to assist the surgeon during the operation. the robotic provides haptic feedback that is transmitted to a surgeon handheld device so that the surgeon can use the haptic feedback to determine what the ball tip probe is in contact with. This method is detailed in this surgical step as an example but is applicable to each surgical step.

Improvements in "Decompression—removal of bone (lamina and/or facet joint)" are made such as Guidance adjustment based on surgeon adjustments in previous procedures based upon image recognition. A method of using image recognition to show a "point of view" from the drill along the drill path. Using Artificial Intelligence pictures are being taken of the drill path and being compared to a historical database of similar surgeries/operations to optimize the drill path for the least amount of potential damage and to improve the confidence of the surgeons using the tool. For example, during a typical decompression surgery 95% of surgeons move the drill two degrees to the left 10 millimeters into the patient, the AI takes control of the robot and automatically applies this movement. This method is detailed in this surgical step as the example is for a decompression, but is applicable to each surgical step.

Improvements in "Decompression—removal of bone (lamina and/or facet joint)" are made such as Machine Learning Method for Guidance Adjustments on Surgery. A method of capturing the data from drill mounted "point of view" camera in which the data is uploaded into a historical database as it is collected and refined to improve the operation of the system in future operations. If there is a known correlation between the current surgery being performed and historical data the AI takes control of the robot to perform the movement. This method is detailed in this surgical step as it is directly related to "Guidance adjustment based on surgeon adjustments in previous procedures based upon image recognition", but is equally applicable in other steps in a spinal surgery.

Improvements in "Decompression—removal of bone (lamina and/or facet joint)" are made such as Method of Machine Learning for Tactile Sensation. A method of collecting data from pressure sensors on a surgical tool (i.e. drill) as well as collecting data from touch sensors and using this data as context to inform the AI system of the surgical robot for the robot to learn a tactile sensation of the operation being performed. Surgical tools with more direct mechanical connections between the end effector and the surgeon's controls are monitored with sensors and imaging systems to determine the type and amplitude of the tactile feedback the surgeon receives during the manipulation of different tissue types during different actions. Those actions are modeled and applied to robotic systems with shared control to provide the best feel for the surgeon while maintaining the precision advantage that robotic systems provide over more traditional surgical tools. This method is detailed in this surgical step as the removal of bone near the nerve tissue is one of the most important applications of this technology, but it is applicable in other steps in the spinal surgery process.

Improvements in "Decompression—removal of bone (lamina and/or facet joint)" are made such as Drill Data Collection for AI System. A method of collecting data from a surgical drill such as RPMs, speed, resistance, and variations of these data points based on the movement of the drill. If the drill is in contact with bone, the data collected would be much different than if the drill was in contact with only soft tissue. This data is collected and used to be incorporated into the AI system so that there is another data point for the AI system to determine what type of tissue the drill is in contact with.

As above, where force and change in force in X,Y,Z are measured and used to inform the surgeon, other robotic parameters such as (1) RPMs, (2) armature current, (3) angle and direction, (4) sound of motor, etc. are measured. As a drill or knife is robotically controlled, the drill or knife would have highly sensitive sensors for (1) RPMs, (2) armature current, (3) angle and direction, (4) sound of motor, etc. These parameters provide real-time robot set of data. These parameters provide data that is collected in many successful operations. The real-time images not only have all the previous metatags discussed, but also have the real sensitive sensor data for (1) RPMs, (2) armature current, (3) angle and direction, (4) sound of motor, etc. Now the system can be trained to show the sensitive sensors changes for (1) RPMs, (2) armature current, (3) angle and direction, (4) sound of motor, etc. going from one tissue type to another. As above the change sensitive sensors for (1) RPMs, (2) armature current, (3) angle and direction, (4) sound of motor, etc. can be used to compare to real-time operations. If the tissues are identified correctly and within range, and the sensitive sensors data for (1) RPMs, (2) armature current, (3) angle and direction, (4) sound of motor, etc. and their associated changes are within range, the images are annotated with virtual information showing that tissues and sensitive sensors data for (1) RPMs, (2) armature current, (3) angle and direction, (4) sound of motor, etc. are in order. If, however, the sensitive sensors data for (1) RPMs, (2) armature current, (3) angle and direction, (4) sound of motor, etc. or the associated changes appear out of normal range, alarms would sound, and automated robotic stops would be done to investigate the out of norm situation. With this system, the surgeon can create a "sensitivity" of sensitive sensors data for (1) RPMs, (2) armature current, (3) angle and direction, (4) sound of motor, etc. at various parts of the operations, so the system may alarm when it approaches a nerve as the sensitive sensors data for (1) RPMs, (2) armature current, (3) angle and direction, (4) sound of motor, etc. and change of sensitive sensors data alarm for (1) RPMs, (2) armature current, (3) angle and direction, (4) sound of motor, etc. is set at a more sensitive level than another part of the operation.

Improvements in "Decompression—removal of bone (lamina and/or facet joint)" are made such as Vibration Cancelling High-Speed Drill. A method of canceling out the haptic feedback caused by the movement of the drill so that a surgeon only receives haptic feedback from the body part that the drill is in contact with. Like noise cancellation technology used in headphones, the drill can have similar vibrations incorporated when the drill is being operated so that there no is no vibrational feedback to the surgeon's hand. The remaining feedback from the operational procedure would be with the body parts that the drill is coming in contact with so that surgeon can better determine if the drill is still in contact with bone or if it is in contact with the canal (or another type of tissue).

Improvements in "Decompression—removal of bone (lamina and/or facet joint)" are made such as Method of Measuring Using Shockwaves Through Surgical Drill. A method of using a seismograph on a surgical drill to send a shockwave through the bone to determine the width or length of the bone to inform the surgeon (or AI drill) on how much bone is left to drill. This could also be used to determine how much of a specific bone (cancellous vs. cortical) is remaining to drill to inform the surgeon or the AI drill.

Improvements in "Decompression—removal of bone (lamina and/or facet joint)" are made such as Shared Laminectomy Procedure. A method of using AI to inform a surgical robot drill to drill down to the lamina in a laminectomy and reach a predetermined point at which the surgical robot will stop and the surgeon will resume the operation.

Improvements in "Decompression—removal of bone (lamina and/or facet joint)" are made such as Laminectomy Using Ultrasound for AI Surgical Robot where the AI surgical robot taking an image, it records an ultrasound to determine if the canal has been reached.

Improvements in "Decompression—removal of bone (lamina and/or facet joint)" are made such as Laminectomy Using Ultrasound for AI Surgical Robot where the AI surgical robot taking an image, it records an CT to determine if the canal has been reached.

Improvements in "Decompression—removal of bone (lamina and/or facet joint)" are made such as Laminectomy Algorithm for AI Surgical Robot Drill Optimization. A variation would be to make variable both the drill speed and the sampling rate that increases as proximity to the canal increases.

Improvements in "Decompression—removal of bone (lamina and/or facet joint)" are made such as Decompression Using AI Surgical Robot is used for laminotomies instead of laminectomies. Additional steps necessary to adjust the process will include further filtering of the patient data from the procedure database based on the volume of the lamina to be removed. This will necessarily include correlation generation not just on the size of the patient's relevant anatomical structures, but also correlations between post-surgical relief levels based upon the degree of and location of lamina removal.

Improvements in "Decompression—removal of bone (lamina and/or facet joint)" are made such as Mapping of Stimulated Nerves for Surgery is a method that overlays a map of the patient's nerves on the anterior-posterior (AP) view. The nerves would be stimulated through some method (i.e. MEP, EMG); the nerve activity would be captured and recorded by sensors placed on the patient. This would enable a robotic surgery to be guided with at least a first image of an electrically stimulated spine. This concept is applicable to multiple steps in a spinal surgery but is described here as an additional method of determining the distance the surgical robot needs to travel through the lamina.

Improvements in "Disc incision and disc removal" are made such as an Ultrasonic Endoscopic Probe for Tissue Identification. A method that uses an ultrasonic, endoscopic probe to determines the remaining tissue type and location during surgery (i.e. discectomy). This will allow surgeons to know what type of tissue is located herein the patient during surgery. This is in addition to or in lieu of the image recognition system used in conjunction with AI to identify the tissue type. The tissue's response to the ultrasonic endoscope is correlated in the same way images are correlated with tissue type definitions.

Improvements in "Fusion—insertion of cage/bone graft" are made such as a Fusion Using AI Surgical Robot. This invention improvement is used for spinal fusion. Additional steps necessary to adjust the process for this will include adjusting the imaging system placement to account for the gap between the end effector (that which is removing lamina in the laminectomy procedure holding the bone graft in this step) and the end of the bone graft. Unlike the laminectomy where the imaging system is focused on the point at which the end effector is in contact with the tissue, in this process the imaging system needs to be focused on where the leading end of the bone graft that is in contact with the tissue. The system will also need to adjust for the switch from tissue removal in the laminectomy to tissue condition and bone graft progress through the desired path. A different, or additional area of focus in this system can be the graft surface and the graft site to check the condition of the contact areas.

Improvements in "Fusion—insertion of cage/bone graft" are made such as Spinal Cage Placement with AI System. An artificial intelligence system that determines the optimal type, size, placement, and application angle of a spinal cage. This will increase accuracy and efficiency, as well as reduce the chance of complications from using the incorrect cage size or placement. This concept combines the planning and cage selection steps detailed in the 3D printed screw guide disclosure with the insertion/placement status steps in 8a.

Improvements in "Fusion—insertion of cage/bone graft" are made such as Artificial Intelligence for Push-Pull Test. An artificial intelligence system that uses force transducers to test the push-pull strength of the spinal cage during insertion. The system will be able to confirm the placement of the spinal cage, reducing the risk of complications postoperatively. This embodiment is based on the push-pull sensors being part of the surgical robot or a stand-alone tool. In 4d the force transducers are part of the cage.

Improvements in "Fusion—insertion of cage/bone graft" are made such as Expandable Spinal Cage with Force Transducers. A system that uses an expandable cage that has multiple force transducers. These transducers can measure force in all directions. The cage can automatically change shape, size, and placement based on the feedback it is receiving from the force transducers. This system will ensure that the amount of force exerted on each component of the change is correct.

Improvements in "Fusion—insertion of cage/bone graft" are made such as Disk Replacement Using AI Surgical Robot. This is a variation on the cage insertion concepts, in which the disk is replaced rather than the cage inserted.

Improvements in "Screw insertion" are made such as Ultrasonic Transducers for Drilling Pilot Hole. This is a method that enables a robot to use ultrasonic transducers to measure its surroundings while it drills the pilot hole for screw insertion. The robot will use an artificial intelligence system to analyze the feedback it receives from the transducers to ensure that there is a sufficient amount of bone surrounding the pilot hole. If the transducers detect too little bone surrounding the pilot hole, the drill will retract and adjust its angle appropriately to fix this problem. This will greatly reduce the risk of a medial or lateral breach while drilling the pilot hole.

Improvements in "Screw insertion" are made such as Laser Projection of Pedicle Cross Section. This is a method of ensuring accurate screw placement by projecting a laser target on the pedicle cross-section that both illuminates the point of insertion, but also the saddle direction necessary for rod placement.

Improvements in "Rod insertion/screw placement" are made such as Instrumentation Using AI Surgical Robot. This improvement is or instrumentation, such as rod and screw insertions/placement. Additional steps necessary to adjust the process for this will include adjusting the imaging system placement to account for the gap between the end effector (that which is removing lamina in the laminectomy procedure, but is holding the hardware in this step) and the end of the hardware. Unlike the laminectomy where the imaging system is focused on the point at which the end effector is in contact with the tissue, in this process the imaging system needs to be focused on where the leading end of the hardware is in contact with the tissue. The system will also need to adjust for the switch from tissue removal in the laminectomy to tissue condition and hardware progress through the desired path. Wider field of view imaging may be advantageous in this application to track the hardware's relative position to different tissues, in addition to or in lieu of, the point of contact imaging that is done in the laminectomy. For example, the system may strive to keep the rod being inserted a minimum distance from the skin surface while maneuvering it into its final position.

Improvements in "Flexible Tube for Rod Placement" are made such as a Flexible Tube for Rod Placement which is a method for inserting a flexible tube into the patient to use as a guide for placing a rod. The flexible tube has a working end; the direction that the working end is moving can be changed by the surgeon. By using a flexible tube, it is easier to connect all the U-shaped equipment in the patient.

Improvements in "Guidance and Navigation" are made such as a Nerve conduction for nerve location in robotic navigation which is a method that uses nerve conduction study to inform the robot of its proximity to the nerve by sensing electrical conduction proximate to the end effector.

Improvements in "Imaging" are made such as using Motion and Sensor Context Data to Inform AI using a method of collecting sensor data from an operating room (i.e. visual, audio, or environmental data) and collecting motion data from the tool being used to perform the surgery. The sensor data and motion data is used as context data to inform the Artificial Intelligence system of the robot to enhance the learning of the robot Improvements in "Imaging" are made such as using Electric Nerve Stimulation for Diagnosing Nerve Injuries using a non-invasive method for finding injured nerves or disease in a patient using the stimulation of nerves with electricity. This method could replace the electromyogram, which is considered a very painful surgery to find injured nerves.

Improvements in "Imaging" are made such as using a Wireless EEG for Diagnosis by using a wireless EEG to diagnose diseases and disorders based on patient's brain activity. This could be used to diagnose various diseases and disorders, including ADHD, depression, etc.

Improvements in "Imaging" are made such as using Wireless EEG Images in Specific Steps for Surgical Procedures specifically implementing a method for using imaging from a wireless EEG during specific steps in a surgical procedure in real-time. For example, imaging from a wireless EEG may be used with x-ray images, bone position, and the position of a drill for specific steps throughout a procedure that involves inserting a screw into a patient's spine.

Improvements in "Imaging" are made such as using a Laser Overlay on AP view for Incision Site Location specifically using a method for using a laser that overlays the location of the incision made by the surgeon onto the anterior-posterior (AP) view. This invention places the optical location of the incision over the AP view, which can illustrate whether the incision should be changed (i.e. making it a bit longer) on a computer. The laser could highlight on the patient's back where the change (i.e. the lengthening) of the incision should be made.

Improvements in "invasiveness" are made such as using a Single Port with Multiple Arms, which uses a device that has a single port that expands into multiple arms when the robot is deployed inside of the abdomen. This allows for only one arm to be inserted into the patient's body instead of having multiple arms.

Improvements in "planning and mapping" are made such as using a Machine Learning Workflow Optimization for Surgical Robot, using a method of workflow optimization by collecting data throughout a surgical process and then using the collected data for the following workflow. This data can be incorporated into an AI system to provide surgical robot machine learning capabilities on the surgical procedures.

Improvements in "planning and mapping" are made such as using a Surgical Path Mapping for Neurosurgery, which provides a means for mapping the surgical path for neurosurgery procedures that minimize damage through artificial intelligence mapping. The software for artificial intelligence is trained to track the least destructive pathway. The neurosurgeon makes the initial incision based on a laser marking on the skin that illuminates the optimal site. Next, a robot makes a tiny hole and inserts a guide wire that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or AI system. The comparison can be used to determine next steps in a procedure and/or further train the AI system.

Improvements in "post-operative spinal surgery" are made such as using a Restenosis Sensor in a method to insert a sensor into the patient that measures pressure, bone growth, and/or force. The sensor would be inserted after a laminectomy and used to help determine if the patient has restenosis based on the data it collects. This will increase the accuracy of restenosis diagnosis.

Improvements in "post-operative spinal surgery" are made such as Robot for Monitoring Surgery Recovery in the Epidural using a method that enables a small robot to travel in the epidural space. This robot can collect information pertaining to the patient's recovery process to determine if the surgery was successful, and if not, what complications occurred.

Improvements in "post-operative spinal surgery" are made such as a Temperature Sensor for Monitoring Post-Operative Recovery using a method that enables a biodegradable temperature sensor to be attached to an implant that was inserted into the patient during surgery. This sensor will be able to detect the onset of post-operative infection during the first weeks of recovery. The sensor will naturally dissolve once the period of concern for infection is over.

Improvements in "post-operative spinal surgery" are made such as a Biodegradable, Biomarker Sensor for Detecting Infection using a biodegradable, biomarker sensor that can determine if the tissue becomes infected post-operatively. If it detects an infection, a notification is sent to the patient and/or the surgeon. This sensor is placed onto tissue that may become infected using a probe during surgery. More than one sensor may be placed depending on how many areas of potential infection there are in the patient.

Improvements in "support surgical tools" are made such as a Ball Probe with an Accelerometer using a ball probe that has an accelerometer. This probe can then collect information pertaining to force in areas of interest. For example, it can use the accelerometer data to measure bumps on a tissue surface and the AI determines when a threshold has been crossed that the amplitude of the bumps indicates the surgery is complete Improvements in "support surgical tools" are made such as a Biomolecular Tagging of a Tumor using a method for bio molecularly tagging a tumor for surgery. This includes a probe with biomarker on it to tag specific types of tissue (i.e. muscle). This mark will light up with LED when it is on the specified tissue type (i.e. muscle). The marker in this system will be able to recognize what type of tissue it is touching and then be able to mark it accordingly. This will improve robotic vision systems during a robotic surgery.

Improvements in "support surgical tools" are made such as a Graphene Probe for Tagging Different Tissue Types, using a method that enables graphene to be incorporated into a probe that can mark different tissue types. This marker will recognize what type of tissue it is touch and be able to mark the tissue accordingly.

Improvements in "support surgical tools" are made such as a Rod Placement prior to Screw Placement using a method that involves inserting the rod prior to inserting the screw. The rod is designed to have a hole and phalanges. The entirety of the operation is done through the rod. When the screw is inserted into the rod, the rod is moved one screw length to keep the rod solid. This allows the rod to be connected to all the screws being inserted into the patient. This method allows for the rod's positioning to be optimized.

Improvements in "user interfaces in the spinal surgery invention" are made such as a Robotic Scalpel with Voice-Command using a robotic scalpel that responds to voice-commands (i.e. "scalpel—2 millimeters" would move the scalpel 2 millimeters).

Figure 6:
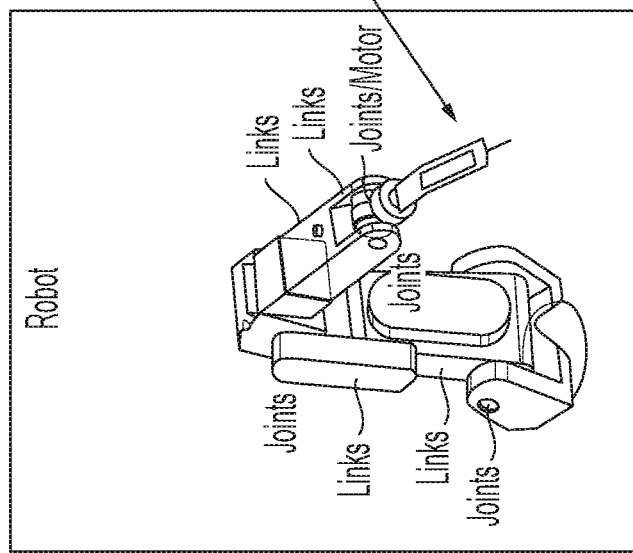
FIG. 6 illustrates a robotic system, according to an embodiment.

FIG. 6 illustrates a robotic system, according to an embodiment. The robotic system can be used to perform the procedures disclosed herein. The robotic system can include one or more joints, links, grippers, motors, and effector interfaces, or the like. The configuration and functionality of the robotic system can be selected based on the procedures to be performed. A robotic system with a high number of degrees of freedom can be used to perform complicated procedures whereas a robotic system with a low number of degrees of freedom can be used to perform simple procedures.

Figure 7:
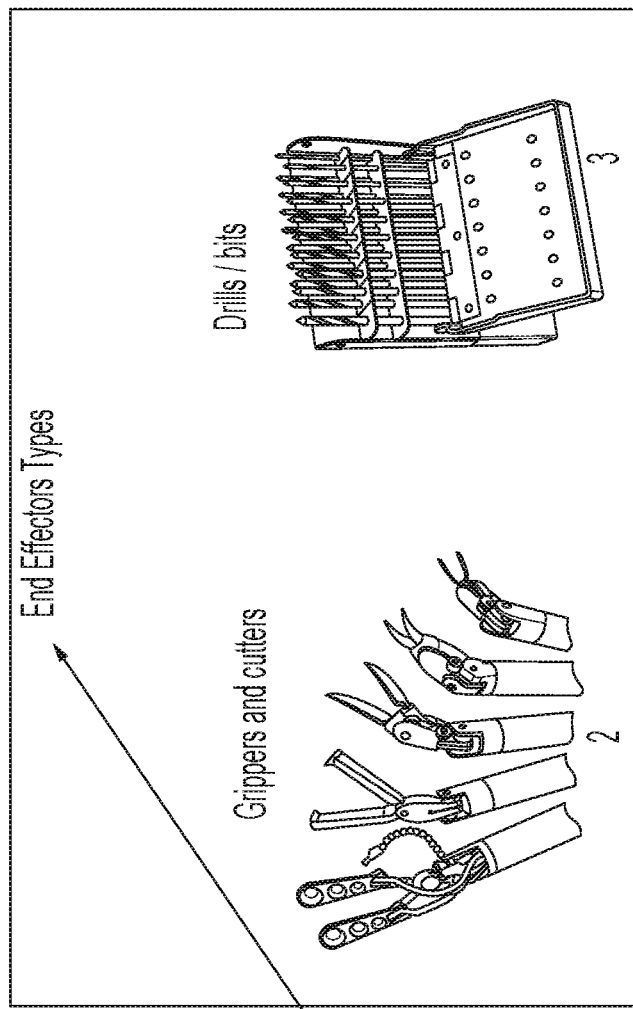
FIG. 7 illustrates end effectors, according to an embodiment.

FIG. 7 illustrates end effectors, according to an embodiment. The effectors can be installed in the robotic system of FIG. 6 or other robotic systems disclosed herein. The end effectors can include, without limitation, robotic grippers, cutting instruments (e.g., cutters, scalpels, or the like), drills, cannulas, reamers, rongeurs, scissors, clamps, or the like. The number and configuration of end effectors can be selected based on the configuration of the robotic system and the procedure to be performed. The AI system can select end effectors to perform one or more the steps in a surgical procedure.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Various systems, methods, and techniques described above provide a number of ways to carry out the invention. Of course, it is to be understood that not necessarily all objectives or advantages described may be achieved in accordance with any particular embodiment described herein and may depend on the procedures to be performed, robotic system, and end effectors to be used. Thus, for example, those skilled in the art will recognize that the methods may be performed in a manner that achieves or optimizes one advantage or group of advantages as taught herein without necessarily achieving other objectives or advantages as may be taught or suggested herein. Furthermore, the skilled artisan will recognize the interchangeability of various features from different embodiments disclosed herein and disclosed in U.S. App. No. 62/636,046; U.S. application Ser. No. 15/291,357; U.S. application Ser. No. 16/001,055; U.S. application Ser. No. 16/012,464; U.S. application Ser. No. 16/015,486; U.S. application Ser. No. 16/023,014; and U.S. application Ser. No. 16/028,618, and all of these applications are incorporated herein by reference in their entireties. For example, guiding techniques, display techniques, endoscope control in these applications can be incorporated into the systems disclosed herein. Similarly, the various features and acts discussed above, as well as other known equivalents for each such feature or act, can be mixed and matched by one of ordinary skill in this art to perform methods in accordance with principles described herein.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method implemented in a computing system for at least partially controlling a robotic surgical apparatus to perform surgical actions, the method comprising:
   obtaining a first image of a region of interest associated with a subject;
   identifying a type of tissue shown in the first image based, at least in part, on a neural network model trained on an image training set;
   in response to determining that the identified type of tissue belongs to a set of targeted types, causing the robotic surgical apparatus to perform a first surgical action with respect to the region of interest in accordance with a surgical plan;
   obtaining a second image of the region of interest after completion of the first surgical action; and
   in response to a failure to identify a type of tissue shown in the second image based, at least in part, on the neural network model:
      presenting the second image to a user; and
      receiving an input from the user indicating a type of tissue shown in the second image.

2. The method of claim 1, further comprising:
   in response to determining that the user indicated type of tissue belongs to the set of targeted types:
      updating the image training set with the second image; and
      causing the surgical apparatus to perform a second surgical action with respect to the region of interest in accordance with the surgical plan.

3. The method of claim 2, further comprising causing the neural network model to be re-trained based, at least in part, on the updated image training set.

4. The method of claim 1, wherein the first surgical action includes removal of a portion of tissue.

5. The method of claim 1, wherein the region of interest is in front of an end effector of the robotic surgical apparatus.

6. The method of claim 1, wherein the image training set includes at least a plurality of pre-collected images and metadata of tissue type associated with each pre-collected image.

7. The method of claim 1, wherein an end effector of the robotic surgical apparatus is changed after completion of the first surgical action.

8. The method of claim 1, further comprising enabling a user to halt the execution of the method in response to a fail-safe trigger.

9. The method of claim 8, wherein the fail-safe trigger is based on at least one of a time sequence of identified tissue types, a length of time between identification of normal tissue types, a trend of probability associated with tissue type identification, or a quality of obtained image.

10. A non-transitory computer-readable storage medium storing content that, when executed by one or more processors, causes the one or more processors to perform actions including:
   obtaining a first image of a region of interest associated with a surgery subject;
   identifying a type of tissue shown in the first image based, at least in part, on a neural network model;
   in response to determining that the identified type of tissue belongs to a set of targeted types, causing a robotic surgical apparatus to perform a first surgical action with respect to the region of interest in accordance with a surgical plan; and
   obtaining a second image of the region of interest after completion of the first surgical action;
   in response to a failure to identify a type of tissue shown in the second image based, at least in part, on the neural network model:
      presenting the second image to a user; and
      receiving an input from the user indicating a type of tissue shown in the second image.

11. The computer-readable storage medium of claim 10, wherein the identified type of tissue includes at least one of bone, cartilage, ligaments, disc, solid organs, or aberrant tissue.

12. The computer-readable storage medium of claim 10, wherein the first surgical action is performed by a first end effector of the robotic surgical apparatus.

13. The computer-readable storage medium of claim 12, wherein the actions further include determining to replace the first end effector with a second end effector in accordance with the surgical plan.

14. The computer-readable storage medium of claim 10, wherein a first end effector of the robotic surgical apparatus includes at least one of a robotic gripper, cutting instrument, cannula, reamer, rongeur, scissors, retractor tube, incision marker, bone removal tool, or skin and/or muscle fascia incision tool.

15. A system for at least partially controlling a robotic surgical apparatus, comprising:
one or more processors;
at least one display; and
memory storing contents that, when executed by the one or more processors, cause the system to perform actions including:
obtaining one or more first images of a region of interest associated with a surgery subject;
identifying one or more types of tissue shown in the one or more first images based, at least in part, on a neural network model;
displaying the identified one or more types of tissue via a graphical user interface (GUI) on the at least one display;
receiving one or more interactions with the GUI from a user that indicate one or more surgical configurations;
causing a robotic surgical apparatus to perform one or more surgical actions with respect to the region of interest based, at least in part, on the one or more surgical configurations;
obtaining one or more second images of the region of interest after completion of at least one of the surgical actions; and
in response to a failure to identify one or more types of tissue shown in the one or more second images based, at least in part, on the neural network model:
presenting at least one of the second images to the user; and
receiving an input from the user indicating one or more types of tissue shown in the at least one of the second images.

16. The system of claim 15, wherein the at least one display includes a touch screen.

17. The system of claim 15, wherein the one or more surgical configurations include at least one of targeted tissue to be removed or nontargeted tissue to be protected.

18. The system of claim 15, wherein the one or more surgical configurations include at least one of an area of tissue to be removed, a sensitive area to stay away from, or operating parameters of the robotic surgical apparatus.

19. The system of claim 18, wherein the operating parameters of the robotic surgical apparatus further include at least one of penetration depth, operating distance, operating speed, end effector path, hold location, or transition between hold locations.

20. The system of claim 15, wherein displaying the identified one or more types of tissue comprises displaying at least one of an estimated shape, suggested color, or meta-tag data associated with each type of identified tissue.

21. The system of claim 15, wherein displaying the identified one or more types of tissue comprises displaying one or more boundary indicators for indicating at least one of targeted tissue to be removed, protected tissue, delivery instrument placement, or an end effector working space within the subject.

* * * * *

UNITED STATES PATENT AND TRADEMARK OFFICE
CERTIFICATE OF CORRECTION

PATENT NO. : 10,517,681 B2
APPLICATION NO. : 16/288077
DATED : December 31, 2019
INVENTOR(S) : Roh et al.

Page 1 of 1

It is certified that error appears in the above-identified patent and that said Letters Patent is hereby corrected as shown below:

In the Specification

In Column 12, Line 15, delete "yellow+0.5" and insert -- yellow +0.5 --, therefor.

In Column 21, Line 39, after "robot" insert -- . --.

In Column 23, Line 6, after "complete" insert -- . --.

In Column 24, Line 21, delete "and or" and insert -- and/or --, therefor.

Signed and Sealed this
Twenty-eighth Day of April, 2020

Andrei Iancu
*Director of the United States Patent and Trademark Office*